United States Patent [19]

Berneth et al.

[11] Patent Number: 5,208,325
[45] Date of Patent: May 4, 1993

[54] CATIONIC 1,3,4-THIADIAZOLE DYESTUFFS

[75] Inventors: Horst Berneth; Klaus Leverenz, both of Leverkusen, Fed. Rep. of Germany

[73] Assignee: Bayer Aktiengesellschaft, Leverkusen, Fed. Rep. of Germany

[21] Appl. No.: 805,147

[22] Filed: Dec. 11, 1991

[30] Foreign Application Priority Data

Jan. 12, 1991 [DE] Fed. Rep. of Germany ....... 4100810

[51] Int. Cl.$^5$ .................... C09B 29/048; C09B 44/20; C09B 69/06; D06P 1/41
[52] U.S. Cl. ...................... 534/607; 106/22; 106/23; 106/163.1; 106/217; 106/247; 8/437; 162/162; 534/589; 534/613; 534/774; 534/795; 548/138
[58] Field of Search .................. 534/607, 795; 8/437, 8/891; 106/22, 23, 163.1, 217, 496; 162/162

[56] References Cited

U.S. PATENT DOCUMENTS 4,268,438 5/1981 Furstenwerth ................ 534/607 X
4,818,815 4/1989 Moser .................................. 534/607

FOREIGN PATENT DOCUMENTS 0045402 2/1982 European Pat. Off. ............ 534/607
2017134 10/1979 United Kingdom ................ 534/607

Primary Examiner—Floyd D. Higel
Attorney, Agent, or Firm—Sprung, Horn, Kramer & Woods

[57] ABSTRACT

Cationic 1,3,4-thiadiazole dyestuff of the formula

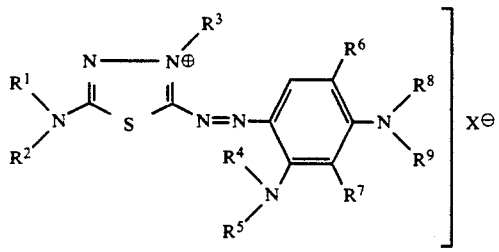

in which
R$^1$ and R$^2$, independently of one another, denote hydrogen, alkyl, alkenyl, cycloalkyl, aralkyl, aryl, a heterocycle, said heterocycle having a direct bond to the nitrogen atom, or being bound through a methylene or ethylene group, or R$^1$ and R$^2$, together with the nitrogen atom to which they are attached form a heterocycle,
R$^3$ denotes alkyl, alkenyl or aralkyl,
R$^4$ denotes hydrogen or alkyl,
R$^5$ denotes acyl,
R$^6$ and R$^7$, independently of one another, denote hydrogen, alkyl, alkoxy, aryloxy or halogen and
R$^8$ and R$^9$, independently of one another, denote hydrogen, alkyl, alkenyl, cycloalkyl, aralkyl, aryl, a heterocycle, said heterocycle having a direct bond to the nitrogen atom, or being bound through a methylene or ethylene group, or R$^8$ and R$^9$, together with the nitrogen atom to which they are attached form a heterocycle, or
R$^6$ and R$^8$ together with the nitrogen to which R$^8$ is attached completes a heterocyclic, said R$^6$ and R$^8$ having a total of from 2 to 4 atoms, one of which can be oxygen or nitrogen, said heterocyclic being either unsubstituted or substituted with from 1 to 3 alkyl groups or (Abstract continued on next page.)

5 Claims, No Drawings

R⁷ and R⁹, together with the nitrogen to which R⁹ is bound completes a heterocyclic, said R⁷ and R⁹ having a total of from 2 to 4 atoms, one of which may be oxygen or nitrogen, said heterocyclic being either unsubstituted or substituted with from 1 to 3 alkyl groups, and $X^e$ denotes an anion and in which all alkyl, alkenyl, cycloalkyl, aralkyl, aryl, alkoxy and heterocyclic radicals present may be substituted by nonionic substitutents, carboxyl groups, ammonium groups and/or pyridinium groups wherein the nonionic substituents are substituents selected from the group consisting of cyano, hydroxyl, fluorine, chlorine, bromine, nitro, alkyl, monoalkylamino, dialkylamino, alkoxy, phenyl, acyloxy, acylamino, alkoxycarbonyl and alkoxycarbonyloxy.

CATIONIC 1,3,4-THIADIAZOLE DYESTUFFS

The present invention relates to cationic 1,3,4thiadiazole dyestuffs of the formula (I)

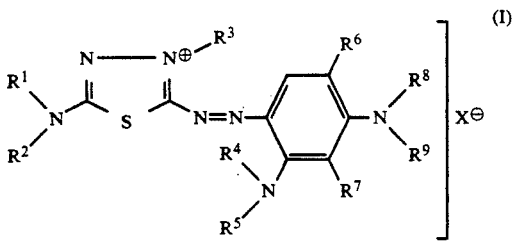

in which
$R^1$ and $R^2$, independently of one another, denote hydrogen, alkyl, alkenyl, cycloalkyl, aralkyl, aryl, a heterocycl which may be bound via a methylene or ethylene bridge or $R^1$ and $R^2$, together with the nitrogen atom in between denote a heterocycle,
$R^3$ denotes alkyl, alkenyl or aralkyl,
$R^4$ denotes hydrogen or alkyl,
$R^5$ denotes an acyl group,
$R^6$ and $R^7$, independently of one another, denote hydrogen, alkyl, alkoxy, aryloxy or halogen and
$R^8$ and $R^9$, independently of one another, denote hydrogen, alkyl, alkenyl, cycloalkyl, aralkyl, aryl, a heterocycle which may bound via a methylene or ethylene bridge or $R^8$ and $R^9$, together with the nitrogen atom in between, denote a heterocycle, in which
$R^6$ and $R^8$ and/or $R^7$ and $R^9$ together can also denote a 2- to 4-membered bridge which may contain an oxygen or nitrogen atom and may be substituted by 1 to 3 alkyl groups and
$X^\ominus$ denotes an anion and
in which all alkyl, alkenyl, cycloalkyl, aralkyl, aryl, alkoxy and heterocyclic radicals present may be substituted by nonionic substituents, carboxyl groups, ammonium groups and/or pyridinium groups, and to their preparation and use and to the corresponding anhydro bases.

Preference is given to cationic 1,3,4-thiadiazole dyestuffs of the formula (I) in which
$R^5$ denotes $SO_2R^{10}$ or $COR^{11}$, in which
$R^{10}$ represents hydrogen, alkyl, alkenyl, cycloalkyl, aralkyl, aryl or a heterocyclic radical, and
$R^{11}$, independently of $R^{10}$, has the same meanings as
$R^{10}$ and can additionally also represent O-alkyl, O-aryl or NH-$R^{10}$.

Examples of nonionic substituents are the nondissociating substituents customary in dyestuff chemistry, such as cyano, hydroxyl, fluorine, chlorine, bromine, nitro, alkyl, monoalkylamino, dialkylamino, alkoxy, phenyl, acyloxy, acylamino, alkoxycarbonyl and alkoxycarbonyloxy.

Examples of acyl radicals are formyl, alkylcarbonyl, alkenylcarbonyl, arylcarbonyl, alkoxycarbonyl, aminocarbonyl, monoalkylaminocarbonyl, dialkylaminocarbonyl, alkylsulphonyl, arylsulphonyl, monoalkylaminosulphonyl, dialkylaminosulphonyl and the radicals of heterocyclic carboxylic and sulphonic acids.

Examples of alkyl radicals, including those in alkoxy and aralkyl radicals, are those having 1 to 8, preferably 1 to 4, C atoms. They can also be branched.

Examples of alkenyl radicals are those having 2 to 6, preferably 2 to 3, C atoms.

Examples of cycloalkyl radicals are those having 4 to 7, preferably 5 to 6, C atoms.

Halogen preferably represents fluorine, chlorine or bromine.

Aryl radicals, including those in aralcyl radicals, are preferably phenyl radicals which are unsubstituted or substituted by 1 to 3 of the nonionic radicals described above and/or a carboxyl group.

Examples of heterocyclic radicals are thienyl, furyl and pyridyl and their partially or completely hydrogenated derivatives. If desired, they may contain 1 to 3 of the nonionic radicals described above.

Preferred anions are colourless, organic and inorganic anions, for example fluoride, chloride, bromide, iodide, perchlorate, tetrafluoroborate, hydroxide, hydrogen sulphate, sulphate, dihydrogen phosphate, hydrogen phosphate, phosphate, hydrogen carbonate, carbonate, methylsulphate, ethylsulphate, cyanate, thiocyanate, tri- and tetrachlorozincate and anions of saturated or unsaturated aliphatic, cycloaliphatic, aromatic or heterocyclic carboxylic and sulphonic acids, such as formate, acetate, hydroxyacetate, cyanoacetate, propionate, hydroxypropionate, oxalate, citrate, lactate, tartrate, the anion of cyclohexahecarboxylic acid, phenyl acetate, benzoate, the anion of nicotinic acid, methanesulphonate, ethanesulphonate, benzenesulphonate, chlorobenzenesulphonate, toluenesulphonate and hexafluorosilicate.

In the case of polyvalent anions, for example sulphate or oxalate, $X^\ominus$ in formula (I) represents one equivalent of such a polyvalent anion.

Furthermore, preference is given to cationic 1,3,4-thiadiazole dyestuffs of the formula (I) in which
$R^1$ and $R^2$, independently of one another, each denote a $C_1-C_8$-alkyl radical which is unsubstituted or substituted by hydroxyl, halogen, cyano, $C_1-C_4$-alkoxy, aminocarbonyl and/or $C_1-C_4$-alkoxycarbonyl, or denote allyl, cyclopentyl, cyclohexyl, an unsubstituted or halogen-, cyano-, $C_1-C_4$-alkyl- and/or $C_1-C_4$-alkoxy-substituted benzyl or phenethyl radical, thienyl, furyl, tetrahydrofuryl, pyridylmethyl or pyridylethyl radical, an unsubstituted or halogen-, cyano-, $C_1-C_4$-alkyl- and/or $C_1-C_4$-alkoxy-substituted phenyl radical, in which $R^2$ can also denote hydrogen, or
$R^1$ and $R^2$, together with the nitrogen atom in between, denote a pyrrolidino, piperidino, piperazino or morpholino radical which may be substituted by up to 4 methyl groups,
$R^3$ denotes unsubstituted or hydroxyl-, halogen-, cyano-, $C_1-C_4$-alkoxy-, aminocarbonyl- and/or $C_1-C_4$-alkoxycarbonyl-substituted $C_1-C_4$-alkyl, allyl or an unsubstituted or halogen-, $C_1-C_4$-alkyl- and/or $C_1-C_4$-alkoxy-substituted benzyl or phenethyl radical,
$R^4$ denotes hydrogen or $C_1-C_4$-alkyl,
$R^5$ denotes $SO_2R^{10}$ or $COR^{11}$,
$R^6$ and $R^7$, independently of one another, are hydrogen, $C_1-C_4$-alkyl, $C_1-C_4$-alkoxy or halogen,
$R^8$ and $R^9$, independently of one another, denote an unsubstituted or hydroxyl-, halogen-, cyano-, $C_1-C_4$-alkoxy-, aminocarbonyl- and/or $C_1-C_4$-alkoxycarbonyl-substituted $C_1-C_4$-alkyl radical, allyl, cyclopentyl, cyclohexyl, an unsubstituted or halogen-, $C_1$-$C_4$-alkyl-, $C_1$-$C_4$-alkoxy-, $C_1$-$C_4$-acylamino- and/or hydroxyl-substituted benzyl, phenethyl or phenyl radical, thienyl, furyl, tetrahydrofuryl, pyridyl, pyridylmethyl or pyridylethyl radical, in which $R^9$ can also denote hydrogen or $R^8$ and $R^9$, together with the nitrogen atom in between, can also denote a pyrrolidino, piperidino, piperazino, morpholino or pyrazolino radical which is unsubstituted or substituted by up to 4 methyl groups, or $R^6$ and $R^8$ and/or $R^7$ and $R^9$ together denote such a bridge that together with the benzene ring to which $R^6$ and/or $R^7$ are bound and the nitrogen atom to which $R^8$ and/or $R^9$ are bound an unsubstituted or $C_1$-$C_4$-alkyl-substituted dihydroindole, tetrahydroquinoline, tetrahydroquinoxaline, tetrahydro-1,4-benzoxazine or julolidine ring is formed, $R^{10}$ and $R^{11}$, independently of one another, each denote hydrogen, unsubstituted or hydroxy-, halogen-, $C_1$-$C_4$-alkoxy- and/or cyano-substituted $C_1$-$C_8$-alkyl, $C_2$-$C_4$-alkenyl, cyclopentyl, cyclohexyl, an unsubstituted or halogen-, cyano-, $C_1$-$C_4$-alkyl- and/or $C_1$-$C_4$-alkoxy-substituted benzyl or phenyl radical, thienyl or pyridyl, in which $R^{11}$ can also denote O-$C_1$- to $C_8$-alkyl, an unsubstituted or halogen-, cyano-, $C_1$-$C_4$-alkyl- and/or $C_1$-$C_4$-alkoxy-substituted benzyloxy or phenyloxy radical or $NHR^{10}$ where $R^{10}$ can have the meaning given here and $X^\ominus$ denotes an anion.

Particular preference is given to cationic 1,3,4-thiadiazole dyestuffs of the formula (I) in which $R^1$ and $R^2$, independently of one another, denote methyl, ethyl, propyl, butyl, methylpropyl, pentyl, methylbutyl, dimethylpropyl, hexyl, hydroxyethyl, hydroxypropyl, chloroethyl, cyanomethyl, cyanoethyl, cyanopropyl, methoxyethyl, ethoxyethyl, methoxypropyl, aminocarbonylmethyl, aminocarbonylethyl, methoxycarbonylmethyl, methoxycarbonylethyl, allyl, cyclohexyl, benzyl, phenethyl, methylbenzyl, chlorobenzyl, methoxybenzyl, phenyl, tolyl, chlorophenyl, anisyl, cyanophenyl, 2- or 4-pyridylmethyl or 2- or 4-pyridylethyl and $R^2$ can also denote hydrogen or $R^1$ and $R^2$, together with the nitrogen atom in between, denote pyrrolidino, piperidino, piperazino or morpholino, $R^3$ denotes methyl, ethyl, propyl, butyl, hydroxyethyl, hydroxypropyl, hydroxybutyl, chloroethyl, cyanomethyl, cyanoethyl, cyanopropyl, methoxyethyl, ethoxyethyl, methoxypropyl, aminocarbonylethyl, methoxycarbonylethyl, ethoxycarbonylethyl, allyl, benzyl, phenethyl, methylbenzyl, chlorobenzyl or methoxybenzyl, $R^4$ denotes hydrogen, $R^5$ denotes $SO_2R^{10}$ or $COR^{11}$, $R^6$ denotes hydrogen, methyl, ethyl, chlorine, methoxy or ethoxy, $R^7$ denotes hydrogen, $R^8$ and $R^9$, independently of one another, denote methyl, ethyl, propyl, butyl, hydroxyethyl, hydroxypropyl, hydroxybutyl, chloroethyl, cyanomethyl, cyanoethyl, cyanopropyl, methoxyethyl, ethoxyethyl, $C_1$-$C_2$-alkylcarbonyloxyethyl, phenylcarbonyloxyethyl, $C_1$- to $C_2$-alkoxycarbonyloxyethyl, cyano-$C_1$- to $C_2$-alkoxyethyl, chlorohydroxypropyl, dihydroxypropyl, methoxypropyl, aminocarbonylethyl, methoxycarbonylethyl, ethoxycarbonylethyl, allyl, benzyl, phenethyl, methylbenzyl, chlorobenzyl, methoxybenzyl, phenyl, methylphenyl, dimethylphenyl, tert.-butylphenyl, chlorophenyl, dichlorophenyl, methoxyphenyl, hydroxymethoxyphenyl, cyanophenyl, acetaminophenyl, 2-thienyl, 2-tetrahydrofuryl, 2- or 4-pyridyl or 2- or 4-pyridylmethyl, in which $R^9$ can also denote hydrogen, or $R^8$ and $R^9$, together with the nitrogen atom in between denote an unsubstituted pyrrolidino, piperidino or morpholino radical or $R^6$ and $R^8$ together denote such a bridge that together with the benzene ring to which $R^6$ is bound and the nitrogen atom to which $R^8$ is bound a dihydroindole, methyldihydroindole, tetrahydroquinoline, methyltetrahydroquinoline, trimethyltetrahydroquinoline or tetrahydro-1,4-benzoxazine ring is formed, $R^{10}$ and $R^{11}$, independently of one another, are each hydrogen, methyl, ethyl, propyl, butyl, hydroxyethyl, hydroxypropyl, hydroxybutyl, cyanoethyl, methoxyethyl, vinyl, allyl, methylvinyl, cyclohexyl, benzyl, chlorobenzyl, phenyl, methylphenyl, dimethylphenyl, chlorophenyl, methoxyphenyl, 2-thienyl or 2-, 3- or 4-pyridyl and $X^\ominus$ denotes a colourless anion.

Very particular preference is given to cationic 1,3,4-thiadiazole dyestuffs of the formula (I), in which $R^1$ and $R^2$, independently of one another, denote methyl, ethyl, propyl, butyl, hydroxyethyl, hydroxypropyl, cyanoethyl, methoxyethyl or ethoxyethyl or $R^1$ and $R^2$, together with the nitrogen atom in between, denote morpholino, $R^3$ denotes methyl, ethyl, hydroxyethyl, hydroxypropyl or cyanoethyl, $R^4$ denotes hydrogen, $R^5$ denotes $COR^{11}$, $R^6$ denotes methyl, chlorine or methoxy, $R^7$ denotes hydrogen, $R^8$ denotes phenyl, methylphenyl, dimethylphenyl, tert.-butylphenyl, chlorophenyl, dichlorophenyl, methoxyphenyl, hydroxyethoxyphenyl, cyanophenyl or acetaminophenyl, $R^9$ denotes hydrogen, $R^{11}$ denotes methyl o ethyl and $X^\ominus$ denotes a colourless anion.

Furthermore, the present invention relates to anhydro bases of the formulae (II) and (III)

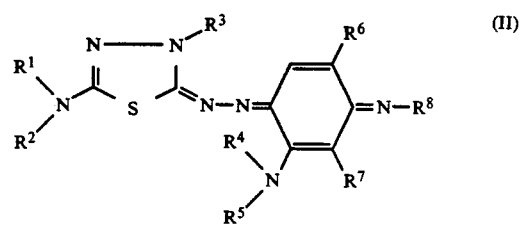

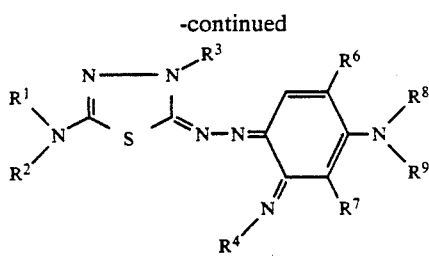
(III)

in which $R^1$ to $R^9$ have the general, exemplary, preferred, particularly preferred and very particularly preferred meaning given in formula (I).

The anhydro bases of the formula (II) and (III) can be obtained from the dyestuffs of the formula (I) by reaction with bases in the presence of a solvent.

Examples of suitable bases are hydroxides, such as sodium hydroxide, potassium hydroxide and calcium hydroxide, oxides, such as magnesium oxide, alcoholates, such as sodium methoxide, sodium ethoxide or sodium tert.-butoxide, amines, such as triethylamine, di- or triethanolamine, piperidine or pyridine or basic ion exchangers based on styrene/divinylbenzene.

Examples of suitable solvents are water, alcohols, such as methanol, ethanol, isopropanol or glycols, ketones, such as acetone or butanone, amides, such as dimethylformamide, dimethylacetamide or N-methylpyrrolidone, nitriles, such as acetonitrile and 3-hydroxypropionitrile, sulphoxides, such as dimethyl sulphoxide, sulphones, such as sulpholane and dimethyl sulphone or N-methylcaprolactam or mixtures thereof.

The anhydro bases of the formulae (II) and (III) are suitable intermediates for the preparation of dyestuffs of the formula (I) containing those anions $X^\ominus$ which cannot be introduced or only in a very complicated manner by one of the preparation processes described below for dyestuffs of the formula (I). In this manner, dyestuffs of the formula (I) can be prepared which obtain special properties by varying the anion $X^\ominus$, for example better solubility and/or better suitability for preparing liquid formulations. To this end, anhydro bases of the formula (II) or (III) can be reacted with the acid of the formula HX whose anion is to be introduced. If desired, the reaction can be carried out in the presence of a solvent and with cooling, at room temperature or temperatures up to the boiling point of the medium.

Examples of solvents are an excess of the acid HX, water, glycols, such as ethylene glycol or propylene glycol, amides, such as ε-caprolactam, nitriles, such as hydroxypropionitrile, the solvents listed above for the preparation of the anhydro bases or mixtures thereof.

Dyestuffs of the formula (I) thus prepared either precipitate from the reaction mixture or produce a stable solution therein.

The anhydro bases of the formulae (II) and (III) themselves are also suitable for dyeing polyester fibres and fabrics and as dyestuffs for sublimation transfer printing, such as described, for example, in EP-A 0,384,040.

The present invention furthermore relates to a process for the preparation of cationic 1,3,4-thiadiazole dyestuffs of the formula (I), which is characterised in that 2-amino-1,3,4-thiadiazoles of the formula (IV)

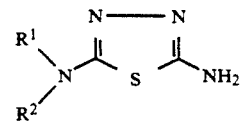
(IV)

in which $R^1$ and $R^2$ have the meaning given in claim 1, are coupled onto m-phenylenediamine derivatives of the formula (V)

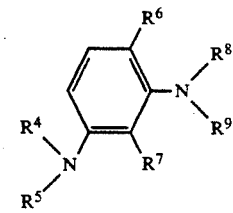
(V)

in which $R^4$ to $R^9$ have the meaning given in claim 1, and the products are then quaternised with compounds of the formula (VI)

$(R^3)X$ (VI)

in which $R^3$ and X have the meaning given in claim 1.

The 2-amino-1,3,4-thiadiazoles of the formula (IV) are disclosed, for example, in DE-A 2,811,258 or are obtainable in analogy thereto. The m-phenylenediamine derivatives of the formula (V) are disclosed, for example, in DE-A 3,840,065, 3,901,839 and 3,906,189 or are obtainable in analogy thereto.

The present invention additionally contains a further process for the preparation of cationic 1,3,4-thiadiazole dyestuffs of the formula (I), which is characterised in that dyestuffs of the formula (VII)

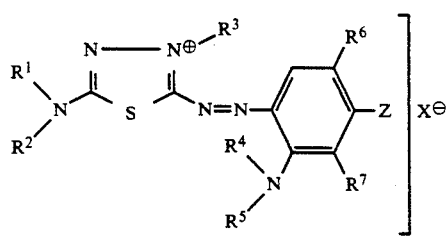
(VII)

in which
$R^1$ to $R^7$ and $X^\ominus$ have the meaning given in claim 1 and
Z represents halogen, hydroxyl, alkoxy, cycloalkoxy, aryloxy, amino or dialkylamino,
are reacted with amines of the formula (VIII)

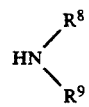
(VIII)

in which $R^8$ and $R^9$ have the meaning given in claim 1.

In formula (VII), Z preferably represents fluorine, chlorine, bromine, hydroxyl, $C_1$–$C_4$-alkoxy, $C_5$–$C_7$-cycloalkoxy, $C_6$–$C_{10}$-aryloxy or NR'R", in which R' and R", independently of one another, represent hydrogen or $C_1$–$C_6$-alkyl.

Compounds of the formula (VII) are new and can obtained, for example, by coupling 2-amino-1,3,4-thiadiazoles of the formula (IV) onto an m-phenylenediamine derivative of the formula (IX)

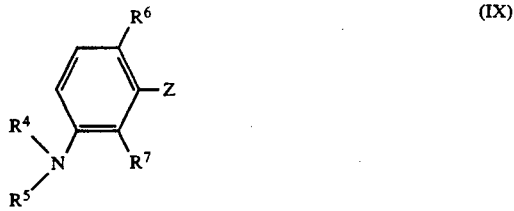

in which $R^4$ to $R^7$ have the meaning given in claim 1 and Z has the meaning given in claim 8, and then quaternising the products with compounds of the formula (VI).

The diazotisations mentioned can be carried out in a manner known per se, for example using nitrosylsulphuric acid in 80 to 90% strength by weight phosphoric acid or in mixtures of such phosphoric acids with acetic acid, propionic acid and/or sulphuric acid. The couplings mentioned can also be carried out in a manner known per se, for example in an acidic medium which may be aqueous or aqueous-organic.

The diazotisations and couplings can also be carried out simultaneously by other processes known per se, for example by reacting compounds of the formula (IV) and compounds of the formula (V) or (IX) jointly in an acidic medium with, for example, sodium nitrite. Examples of suitable acidic media are aqueous mineral acids or organic acids or mixtures thereof, examples of suitable mineral acids being hydrochloric acid, sulphuric acid or phosphoric acid and examples of suitable organic acids being formic acid, acetic acid or propionic acid. Carbon dioxide liquefied under pressure can also serve as the acidic medium.

Examples of suitable quaternising agents are alkyl halides, halogenoacetamides, β-halogenopropionitriles, halogenohydrins, alkylene oxides, alkyl esters of sulphuric acid, alkyl esters of organic sulphonic acids, nitriles, amides and esters of α,β-unsaturated carboxylic acids, alkoxyalkyl halides and vinylpyridines. Examples are: methyl chloride, methyl bromide, methyl iodide, benzyl chloride, benzyl bromide, chloroacetamide, β-chloropropionitrile, ethylene chlorohydrin, dimethyl sulphate, diethyl sulphate, methylbenzenesulphonate, ethyl benzenesulphonate, methyl toluenesulphonate, ethyl toluenesulphonate, propyl toluenesulphonate, allyl chloride, allyl bromide, ethylene oxide, propylene oxide, acrylonitrile, acrylic acid, acrylamide, methyl acrylate, 2- and 4-vinylpyridine, sulpholene (=1,1-dioxo-2,5-dihydrothiophene), epichlorohydrin, styrene oxide, dimethyl methylphosphonate and allyl phosphate.

The quaternisations mentioned can take place, for example, in an inert organic solvent, in water or in mixtures thereof, it being possible, if desired, to add acid-binding agents, such as magnesium oxide, sodium carbonate, sodium bicarbonate, calcium carbonate or sodium acetate. Examples of suitable organic solvents are hydrocarbons, chlorohydrocarbons, nitrohydrocarbons, nitriles, amides, carboxylic acids, carboxylic anhydrides, ketones and dialkyl sulphoxides, such as benzene, toluene, tetrachloroethane, mono- and dichlorobenzene, nitrobenzene, acetonitrile, propionitrile, dimethylformamide, N-methylpyrrolidone, acetic acid, propionic acid, lactic acid, acetic anhydride, acetone, butanone and dimethyl sulphoxide. The reaction of the dyestuffs of the formula (VII) with amines of the formula (VIII) can also take place in organic solvents, in water or in mixtures thereof. Suitable solvents are those described above. If desired, the reaction can be carried out using an excess of the amine of the formula (VI) at temperatures of, for example, between 0° and 100° C., preferably between 10° and 50° C.

The resulting dyestuffs of the formula (I) either precipitate directly from the solvents and can be isolated, for example by filtering them off, or when water-miscible solvents are used, they can be obtained as solid products which can be filtered off by dilution with water and addition of water-soluble salts, such as sodium chloride or potassium chloride, if desired in the presence of zinc chloride.

The dyestuffs according to the invention of the formula (I) and the dyestuffs of the formula (VII) are highly suitable for dyeing and printing cationically dyeable fibres, preferably polymers and mixed polymers of acrylonitrile and dicyanoethylene, and acid-modified polyamide and polyester fibres, which produces hues having good fastness properties. The dyestuffs can also be used for dyeing and printing cellulose materials treated with tannic acid, paper, silk and leather They are furthermore suitable for producing writing inks, stamping inks and pastes for ball-point pens and can also be used in flexographic printing.

Dyeing of, for example, acrylonitrile polymers and mixed polymers can take place, for example, from a weakly acidic liquor, in which the dyebath is preferably entered at 40° to 60° C. and the material is then dyed at the boiling temperature. It is also possible to dye at temperatures above 100° C. under pressure. Furthermore, the dyestuffs according to the invention can be used to . prepare spinning solutions for the dyeing of polyacrylonitrile-containing fibres.

The dyeings on polyacrylonitrile materials produced by the dyestuffs according to the invention of the formula (I) are distinguished by very good light, wet and rubfastness properties and by a very high affinity to the fibre.

Dyestuffs according to the invention can be used individually, in mixtures with one another or in mixtures with other dyestuffs.

Finally, the present invention also relates to cationically dyeable fibres, cellulose materials treated with tannic acid, paper, silk, leather, paste for ball-point pens, writing inks and stamping inks which are characterised in that they contain at least one cationic 1,3,4-thiadiazole dyestuff of claim 1.

EXAMPLES

Example 1

41.7 g of 2-amino-5-diisopropylamino-1,3,4-thiadiazole (96% strength by weight) and 42.05 g of 3-acetylamino-N,N-diethylaniline were dissolved in 200 ml of glacial acetic acid. A solution of 13.8 g of sodium nitrite in 24 g of water was added dropwise at 25° C. over a period of 90 minutes, and the mixture was then stirred at room temperature overnight. 41.8 g of dimethyl sulphate were then added dropwise at 35° to 40° C. over a period of 3 hours, followed by the addition of 16.2 g of anhydrous sodium acetate. After 2 hours at 40° C., the mixture was stirred at room temperature overnight, poured into 500 ml of water and filtered. 100 ml of 2-molar zinc chloride solution and 450 ml of saturated sodium chloride solution were added to the filtrate. The mixture was stirred overnight, filtered off with suction, and the product was dried in vacuo, giving 112.6 g of blue crystals of the formula (I) where $R^1=R^2=$isopropyl, $R^3=CH_3$, $R^4=R^6=R^7=H$, $R^5=COCH_3$, $R^8=R^9=C_2H_5$ and $X^{\ominus}=ZnCl_3^-$. $\lambda_{max}$ value, measured in 10% strength acetic acid, was 596 nm.

The dyestuff thus obtained dyed polyacrylonitrile slightly reddish blue.

Example 2 a) 20.9 g of 2-amino-5-diisopropylamino-1,3,4-thiadiazole (96% strength by weight) were dissolved in a mixture of 50 ml of glacial acetic acid, 15 g of 48% strength by weight sulphuric acid and 5 g of 85% strength by weight phosphoric acid. 34 g of 40% strength by weight nitrosylsulphuric acid (in sulphuric acid) were added dropwise at $-5°$ C. over a period of 45 minutes.

b) 15.3 g of 4-aminoveratrole were dissolved in 100 ml of glacial acetic acid, and 10.2 g of acetic anhydride were added dropwise. This was followed by stirring at room temperature for another hour.

c) The diazo solution from a) was run into the solution of 4-acetaminoveratrole from b) at 0° C., and stirring of the mixture at room temperature was then continued for another 2 hours.

d) 32.8 g of anhydrous sodium acetate were added, and 30.4 ml of dimethyl sulphate were then added dropwise at 40° C. over a period of 3 hours, 8.2 g of anhydrous sodium acetate was added, and the mixture was stirred at 40° C. for another 2 hours.

e) 18.6 g of aniline were added at room temperature, and the pH brought to 3.7. After stirring overnight, 100 ml of saturated sodium chloride solution were added. The product was filtered off with suction and then washed with sodium chloride solution. After drying, 49.7 g of a blue powder of the formula (I) where $R^1=R^2=$isopropyl, $R^3=CH_3$, $R^4=R^6=R^7=R^8=H$, $R^5=COCH_3$, $R^9=$phenyl and $X^{\ominus}=Cl^{\ominus}$ were obtained. The $\lambda_{max}$ value, measured in 10% strength by weight acetic acid, was 616 nm.

The dyestuff dyed polyacrylonitrile and wood-containing paper greenish blue.

The following examples (see Tables 1 to 5) were carried out analogously to Examples 1 and 2:

TABLE 1

In all examples listed here, compounds of the formula (I) where $R^1 = R^2 =$ isopropyl, $R^3 = CH_3$, $R^4 = R^7 = H$, $R^5 = COCH_3$, $R^6 = OCH_3$ and $X^{\ominus}= ZnCl_3^{\ominus}$ were prepared.

| Example No. | $N(R^8)(R^9)$ | $\lambda_{max}$(nm) | Procedure analogous to Example |
|---|---|---|---|
| 3 | $N(CH_2-CH_2-OH)_2$ | 566 | 2 |
| 4 | $N(C_2H_5)_2$ | 606 | 1 |
| 5 | $NHC_4H_9$ | 592 | 2 |
| 6 | NH—cyclohexyl | 593 | 2 |
| 7 | morpholino | 622 | 2 |
| 8 | piperidino | 606 | 1 |
| 9 | —NH—C$_6$H$_4$—Cl | 618 | 2 |
| 10 | N(CH$_3$)(C$_6$H$_5$) | 618 | 2 |
| 11 | NH—C$_6$H$_4$—OCH$_3$ | 618 | 2 |

TABLE 2

In all examples listed here, compounds of the formula (I) where $R^1 = R^2 =$ isopropyl, $R^3 = CH_3$ and $R^4 = R^7 = H$ were prepared.

| Example No. | $N(R^8)(R^9)$ | $R^5$ | $R^6$ | $X^{\ominus}$ | $\lambda_{max}$(nm) | Procedure analogous to Example |
|---|---|---|---|---|---|---|
| 12 | $N(CH_3)_2$ | $COCH_3$ | $OC_2H_5$ | $ZnCl_3^{\ominus}$ | 610 | 2 |
| 13 | $NHCH_2CH_2OC_2H_5$ | $COCH_3$ | $OCH_3$ | $CH_3OSO_3^{\ominus}$ | 594 | 2 |
| 14 | $N(CH_3)_2$ | $COCH_3$ | $CH_3$ | $CH_3OSO_3^{\ominus}$ | | 1 |
| 15 | NH—C$_6$H$_4$—CH$_3$ | $COCH_3$ | $OCH_3$ | $Cl^{\ominus}$ | 620 | 2 |
| 16 | NH—C$_6$H$_4$—CH$_3$ | $COCH_3$ | $OCH_3$ | $Cl^{\ominus}$ | 618 | 2 |

TABLE 2-continued

In all examples listed here, compounds of the formula (I) where $R^1 = R^2$ = isopropyl, $R^3 = CH_3$ and $R^4 = R^7 = H$ were prepared.

| Example No. | $\begin{array}{c} R^8 \\ N \\ R^9 \end{array}$ | $R^5$ | $R^6$ | $X^\ominus$ | $\lambda_{max}$(nm) | Procedure analogous to Example |
|---|---|---|---|---|---|---|
| 17 |  NH—(2,5-dimethylphenyl) | COOCH$_3$ | OCH$_3$ | Cl$^\ominus$ | 619 | 2 |
| 18 | 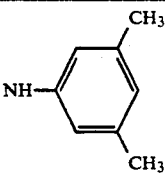 NH—(3,4-dimethylphenyl) | COCH$_3$ | OCH$_3$ | Cl$^\ominus$ | 620 | 2 |
| 19 | 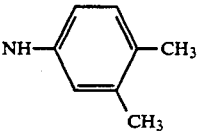 NH—(4-ethylphenyl) | COCH$_3$ | OCH$_3$ | Cl$^\ominus$ | 620 | 2 |
| 20 | 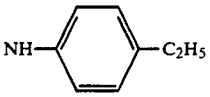 NH—(4-tert-butylphenyl) | COCH$_3$ | OCH$_3$ | Cl$^\ominus$ | 622 | 2 |
| 21 | 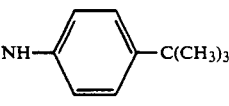 NH—(4-cyclohexylphenyl) | COCH$_3$ | OCH$_3$ | Cl$^\ominus$ | 621 | 2 |
| 22 | 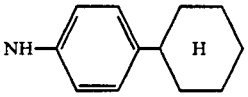 NH—(3,4-dimethoxyphenyl) | COC$_2$H$_5$ | OCH$_3$ | Cl$^\ominus$ | 626 | 2 |
| 23 | 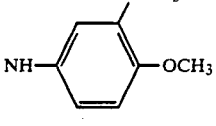 NH—(4-ethoxyphenyl) | CO—NH-Phenyl | OCH$_3$ | Cl$^\ominus$ | 622 | 2 |
| 24 | 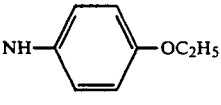 NH—(4-(2-hydroxyethoxy)phenyl) | COCH$_3$ | OCH$_3$ | Cl$^\ominus$ | 621 | 2 |
| 25 | 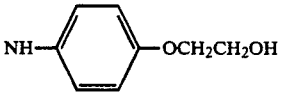 NH—(4-acetylphenyl) | COCH$_3$ | OCH$_3$ | Cl$^\ominus$ | 628 | 2 |
| 26 | 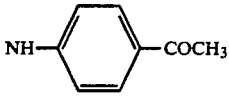 NH—(4-carbamoylphenyl) | COC$_3$H$_7$ | OCH$_3$ | CH$_3$OSO$_3^\ominus$ | 625 | 2 |
| 27 | 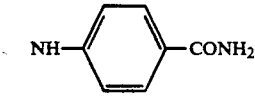 NH—(4-carboxyphenyl) | COCH$_3$ | OCH$_3$ | Cl$^\ominus$ | 626 | 2 |

TABLE 2-continued
In all examples listed here, compounds of the formula (I) where $R^1 = R^2 =$ isopropyl, $R^3 = CH_3$ and $R^4 = R^7 = H$ were prepared.
| Example No. | $\begin{array}{c} R^8 \\ \diagdown N \diagup \\ R^9 \end{array}$ | $R^5$ | $R^6$ | $X^\ominus$ | $\lambda_{max}$(nm) | Procedure analogous to Example |
|---|---|---|---|---|---|---|
| 28 |  | $COCH_3$ | $OCH_3$ | $Cl^\ominus$ | | 2 |

TABLE 3

In all examples listed here, compounds of the formula (I) where $R^4 = R^7 = H$ were prepared.

| Example No. | $\overset{R^8}{\underset{R^9}{N}}$ | $\overset{R^1}{\underset{R^2}{N}}$ | $R^3$ | $R^5$ | $R^6$ | $X^\ominus$ | $\lambda_{max}$(nm) | Procedure analogous to Example |
|---|---|---|---|---|---|---|---|---|
| 29 | piperidine (N-linked) | N(CH(CH₃)₂)₂ | CH₂CH₂CN | COCH₃ | OCH₃ | ZnCl₃⊖ | 628 | 1 |
| 30 | 2-COOH-anilino (NH) | N(C₂H₅)₂ | CH₃ | COCH₃ | OCH₃ | ZnCl₃⊖ | | 2 |
| 31 | 4-NHCOCH₃-anilino (NH) | N(CH(CH₃)₂)₂ | CH₃ | COCH₃ | OCH₃ | Cl⊖ | 621 | 2 |
| 32 | N(C₂H₅)₂ | 4-OCH₃-anilino (NH) | CH₃ | COCH₃ | H | ZnCl₃⊖ | | 1 |
| 33 | anilino (NH) | NH—CH₂—CH₂—CN | C₃H₇ | COCH₃ | OCH₃ | Cl⊖ | | 2 |
| 34 | 4-OH-anilino (NH) | piperidine (N-linked) | CH₃ | COCH₃ | OCH(CH₃)₂ | CH₃OSO₃⊖ | 620 | 2 |
| 35 | 2-OH-anilino (NH) | piperidine (N-linked) | CH₃ | COCH₃ | OCH₃ | CH₃OSO₃⊖ | 616 | 2 |

TABLE 3-continued

In all examples listed here, compounds of the formula (I) where $R^4 = R^7 = H$ were prepared.

| Example No. | $R^8\text{-}N\text{-}R^9$ | $R^1\text{-}N\text{-}R^2$ | $R^3$ | $R^5$ | $R^6$ | $X^\ominus$ | $\lambda_{max}$(nm) | Procedure analogous to Example |
|---|---|---|---|---|---|---|---|---|
| 36 | NH—C₆H₄—NH₂ (para) | piperidine | C₂H₅ | COCH₃ | OCH₃ | C₂H₅OSO₃⁻ | 637 | 2 |
| 37 | NH—C₆H₄—NH₂ (ortho) | piperidine | CH₃ | COCH₃ | OCH₃ | ZnCl₃⁻ | 614 | 2 |
| 38 | NH—C₆H₅ | N(CH₃)₂ | CH₃ | COCH₃ | OCH₃ | Cl⁻ | 610 | 2 |
| 39 | N(C₂H₅)₂ | N(CH₃)₂ | CH₂CH₂CN | COCH₃ | H | ClO₄⁻ | 596 | 1 |
| 40 | N(C₂H₅)₂ | N(CH₃)₂ | CH₂CH₂CONH₂ | COCH₃ | H | Cl⁻ | 596 | 1 |
| 41 | N(C₂H₅)₂ | N(CH₃)₂ | CH₂—CH(OH)—CH₃ | COCH₃ | H | Cl⁻ | 596 | 1 |
| 42 | NH—C₆H₃(Cl)₂ | morpholine | CH₃ | COC₂H₅ | OCH₃ | Cl⁻ | | 2 |

TABLE 4

In all examples listed here, compounds of the formula (I) where $R^1 = R^2 =$ isopropyl and $R^4 = R^7 =$ H were prepared.

| Example No. | $R^3$ | $R^5$ | $R^6$ | $\text{N} \begin{smallmatrix} R^8 \\ R^9 \end{smallmatrix}$ | $X^\ominus$ | $\lambda_{max}$(nm) or colour | Procedure analogous to Example |
|---|---|---|---|---|---|---|---|
| 43 | $CH_3$ | $SO_2CH_3$ | $OCH_3$ | 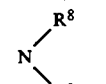 | $Cl^\ominus$ | 609 | 2 |
| 44 | $CH_3$ | $SO_2CH_3$ | $OCH_3$ | 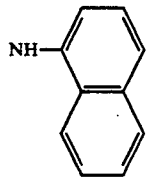 | $ClO_4^\ominus$ | 625 | 2 |
| 45 | $CH_3$ | $SO_2CH_3$ | $OC_2H_5$ |  | $Cl^\ominus$ | 624 | 2 |
| 46 | $CH_3$ | $SO_2CH_3$ | $OCH_3$ |  | $Cl^\ominus$ | 610 | 2 |
| 47 | $C_2H_5$ | $SO_2CH_3$ | $OCH_3$ |  | $Cl^\ominus$ | 617 | 2 |
| 48 | $CH_3$ | $SO_2C_2H_5$ | $OCH_3$ | 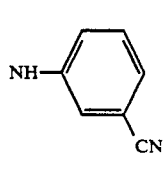 | $CH_3OSO_3^\ominus$ | 609 | 2 |
| 49 | 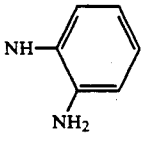 | $SO_2C_2H_5$ | $OCH_3$ | 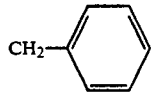 | $Cl^\ominus$ | 615 | 2 |
| 50 | $CH_3$ | $SO_2C_2H_5$ | $OCH_3$ | 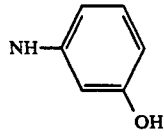 | $ZnCl_3^\ominus$ | 611 | 2 |
| 51 | $CH_3$ | $SO_2CH_3$ | $OCH_3$ | 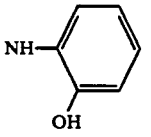 | $ZnCl_3^\ominus$ | 614 | 2 |
| 52 | $CH_3$ | $SO_2CH_3$ | $OCH_3$ |  | $ZnCl_3^\ominus$ | 595 | 2 |

TABLE 4-continued

In all examples listed here, compounds of the formula (I) where $R^1 = R^2 =$ isopropyl and $R^4 = R^7 = H$ were prepared.

| Example No. | $R^3$ | $R^5$ | $R^6$ | $\begin{array}{c}R^8\\ \diagdown\\ N\\ \diagup\\ R^9\end{array}$ | $X^\ominus$ | $\lambda_{max}$(nm) or colour | Procedure analogous to Example |
|---|---|---|---|---|---|---|---|
| 53 | CH$_3$ | SO$_2$CH$_3$ | OCH$_3$ | NH—⟨cyclohexyl, H⟩ | ZnCl$_3^\ominus$ | 593 | 2 |
| 54 | CH$_3$ | SO$_2$CH$_3$ | OCH$_3$ | NH—CH$_2$CH$_2$OH | ZnCl$_3^\ominus$ | 591 | 2 |
| 55 | CH$_3$ | SO$_2$CH$_3$ | OCH$_3$ | NH—CH$_3$ | Cl$^\ominus$ | 589 | 2 |
| 56 | CH$_3$ | SO$_2$CH$_3$ | OCH$_3$ | N(CH$_3$)—CH$_2$CH$_2$CN | Cl$^\ominus$ | 618 | 2 |
| 57 | CH$_3$ | SO$_2$CH$_3$ | OCH$_3$ | N(CH$_3$)$_2$ | Cl$^\ominus$ | 613 | 1 |
| 58 | CH$_3$ | COCH=CH$_2$ | OCH$_3$ | N(CH$_3$)—CH$_2$CH$_2$—⟨phenyl⟩ | ZnCl$_3^\ominus$ | greenish blue | 2 |
| 59 | CH$_2$—CH=CH$_2$ | SO$_2$CH$_3$ | H | N(C$_3$H$_7$)$_2$ | ZnCl$_3^\ominus$ | reddish blue | 1 |

TABLE 5

In all examples listed here, compounds of the formula (I) were prepared.

| Example No. | $\overset{R^1}{\underset{R^2}{N-}}$ | $R^3$ | $\overset{R^4}{\underset{R^5}{N-}}$ | $R^7$ | $R^6$ | $\overset{R^8}{\underset{R^9}{N-}}$ | $X^\ominus$ | $\lambda_{max}$(nm) or colour | Procedure analogous to Example |
|---|---|---|---|---|---|---|---|---|---|
| 60 | NH-C$_6$H$_5$ | CH$_3$ | NH—SO$_2$CH$_3$ | H | OCH$_3$ | NH-C$_6$H$_4$-OCH$_3$ | CH$_3$OSO$_3^\ominus$ | 608 | 2 |
| 61 | N(CH$_3$)$_2$ | CH$_3$ | NH—SO$_2$—C$_6$H$_5$ | H | H | N(C$_2$H$_5$)$_2$ | Cl$^\ominus$ | 585 | 1 |
| 62 | N(CH$_3$)$_2$ | CH$_2$CH$_2$CN | NH—SO$_2$C$_4$H$_9$ | H | OCH$_3$ | NH-C$_6$H$_5$ | Cl$^\ominus$ | 610 | 2 |
| 63 | pyrrolidinyl | C$_2$H$_5$ | NH—COCH$_3$ | H | Cl | N(CH$_3$)$_2$ | ZnCl$_3^\ominus$ | reddish blue | 1 |
| 64 | N(CH$_2$—C(OH)H—CH$_3$)$_2$ | CH$_3$ | NH—CO—C$_6$H$_5$ | H |  | —CH(CH$_3$)—C(CH$_3$)(C$_2$H$_5$)—N— | ZnCl$_3^\ominus$ | blue | 1 |
| 65 | N(CH$_3$)—CH$_2$CH=CH$_2$ | CH$_3$ | NH—CO—C$_6$H$_5$ | H |  | N(CH$_2$CH$_2$CN)$_2$ | Cl$^\ominus$ | reddish blue | 1 |
| 66 | N(CH$_3$)—CH$_2$CH$_2$CN | CH$_3$ | N(CH$_3$)—COCH$_3$ | H |  | N(CH$_2$CH$_2$OCOCH$_3$)$_2$ | CH$_3$OSO$_3^\ominus$ | reddish blue | 1 |
| 67 | N(CH$_2$CH$_2$Cl)$_2$ | CH$_2$-C$_6$H$_5$ | NH—SO$_2$CF$_3$ | CH$_3$ | H | N(CH$_3$)$_2$ | Cl$^\ominus$ | reddish blue | 1 |

TABLE 5-continued

In all examples listed here, compounds of the formula (I) were prepared.

| Example No. | R³ | $\begin{array}{c} R^4 \\ \diagdown N \diagup \\ R^5 \end{array}$ | R⁷ | R⁶ | $\begin{array}{c} R^8 \\ \diagdown N \diagup \\ R^9 \end{array}$ | X⁻ | λ_max(nm) or colour | Procedure analogous to Example |
|---|---|---|---|---|---|---|---|---|
| 68 | ![pyridyl-CH₂CH₂-N(CH₃)-] with structure N-CH₂CH₂-(2-pyridyl), CH₃ on N | NH—COCH₃ | H | OCH₃ | N(C₂H₅)₂ | Cl⁻ | greenish blue | 1 |
| 69 | CH₃ | NH—COCH₃ | H | CH₃ | 5-methyl-3,3-dimethyl-pyrazoline (N—CH₃, =N—, C(CH₃), CH₂, C(CH₃)₂) | Cl⁻ | greenish blue | 1 |
| 70 | morpholine (via N); CH₂CH₂-(4-pyridyl) | NH—COCH₃ | H | Cl | 4-(NHCHO)-phenyl-NH— | Cl⁻ | reddish blue | 2 |
| 71 | CH₃ | NH—COC₂H₅ | H | H | —O—CH₂—CH₂—N(CH₃)— (cyclic, attached to phenyl) | Br⁻ | greenish blue | 1 |
| 72 | CH₃ | NHCOCH₃ | H | Cl | NH—CH₂CH₂OCH₃ | Cl⁻ | blue | 1 |
| 73 | CH₃ | NHCOCH₃ | H | CH₃ | NH—phenyl | Cl⁻ | blue | 2 |
| 74 | CH₂CHCH₃ \| OH | NHCOCH₃ | H | CH₃ | N(CH₃)₂ | Cl⁻ | blue | 1 |

In example 68 R¹R²N = N(CH₃)(CH₂CH₂-2-pyridyl)
In example 70 R¹R²N = morpholino; R³ = CH₂CH₂-(4-pyridyl)
In example 71 R¹R²N = anilino (PhNH—); 
In example 72, 73 R¹R²N = N(CH(CH₃)₂)₂
In example 73 R¹R²N also includes N-methyl-cyclohexylamino
In example 74 R¹R²N = N(CH(CH₃)₂)₂

Example 75

Preparation of a Liquid Dyestuff Preparation 10 g of the dyestuff from Example 2 were dissolved in 140 ml of methanol and 10% strength sodium hydroxide solution was added until the blue colour of the solution had disappeared. The precipitated red flakes of the formula (II) where $R^1=R^2=$isopropyl, $R^3=CH_3$, $R^4=R^7=H$, $R^5=COCH_3$, $R^6=OCH_3$ and $R^8=$phenyl were filtered off with suction and dried. The yield was 6.7 g=80% of theory, the melting point 208°–210° C., and $\lambda_{max}$, measured in dimethylformamide, 509 nm.

4.8 g of this compound were dissolved in a mixture of 3.2 g of glacial acetic acid, 2.0 g of lactic acid and 9.0 g of water at 90° C. After cooling, a stable dark blue solution was obtained which contained 30% by weight of the dyestuff of the formula (I) where $R^1=R^2=$isopropyl, $R^3=CH_3$, $R^4=R^7=R^9=H$, $R^5=COCH_3$, $R^6=OCH_3$, $R^8=$phenyl and $X^\ominus=CH_3C(OH)H-COO^\ominus$.

Example 76

Dyeing Procedure for Polyacrylonitrile 0.1 g of the dyestuff obtained according to Example 2 was made into a paste with 2 ml of water with the addition of a small amount of acetic acid and dissolved using 50 ml of hot water. 1.2 g of a condensation product of naphthalenesulphonic acid with formaldehyde were then added, and the mixture was made up to 500 ml with cold water. The pH of this dyeing liquor was brought to 4.5–5 using acetic acid and sodium acetate. In this dyeing liquor, 10 g of piece-good material consisting of polyacrylonitrile fibres were constantly agitated, while the temperature was increased to 100° C. within 30 minutes. The material was dyed at the boiling temperature for 60 minutes, then rinsed with cold water and dried at 60°–70° C.

Example 77

Dyeing Procedure for Wood-containing Paper

To dry pulp consisting of 60% of mechanical pulp and 40% of unbleached sulphite collulose an amount of water was added that the dry solids content was slightly more than 2.5% and ground up to a degree of freeness of 40° SR. The dry solids content of the thickened pulp was then exactly set to 2.5% using water. 5 g of a 0.5% strength by weight aqueous solution of the dyestuff from Example 15 were added to 200 g of this thickened pulp, the mixture was stirred for 5 minutes, 2% of resin size and 4% of alum, relative to the dry pulp, were added, and the mixture was again stirred for a few minutes until it was homogeneous. The pulp suspension was then diluted to 700 ml with water and sheets of paper were produced therefrom in a known manner by squeezing through a hand sheet former. They have an intense greenish blue colour.

The other dyestuffs from Examples 1–75 can be used analogously to Examples 76 and 77.

We claim:

1. A cationic 1,3,4-thiadizole dyestuff of the formula

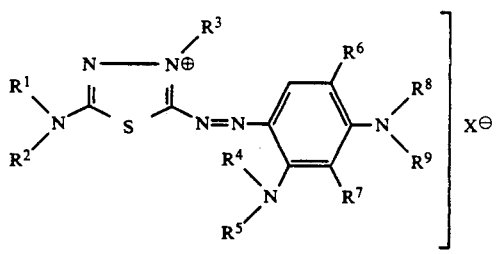

wherein $R^1$ represents a $C_1$–$C_8$-alkyl radical which is unsubstituted or substituted by one or more substitutents selected from the group consisting of hydroxyl, halogen, cyano, $C_1$–$C_4$ alkoxy, aminocarbonyl and $C_1$–$C_4$-alkoxycarbonyl;

or represents allyl, cyclopentyl or cyclohexyl;

or represents a benzyl or phenethyl radical, each of which is unsubstituted or substituted by a substituent selected from the group consisting of halogen, cyano, $C_1$–$C_4$ alkyl and $C_1$–$C_4$ alkoxy;

or represents a thienyl, furyl, tetrahydrofuryl, pyridylmethyl or pyridylethyl radical;

or represents a phenyl radical which is unsubstituted or substituted by one or more substituents selected from the group consisting of halogen, cyano, $C_1$–$C_4$ alkyl, and $C_1$–$C_4$ alkoxy;

$R_2$ represents hydrogen or represents a $C_1$–$C_8$-alkyl radical which is unsubstituted or substituted by one or more substituent selected from the group consisting of hydroxyl, halogen, cyano, $C_1$–$C_4$ alkoxy, aminocarbonyl and $C_1$–$C_4$ alkoxycarbonyl;

or represents allyl, cyclopentyl or cyclohexyl;

or represents a benzyl or phenethyl radical, each of which is unsubstituted or substituted by a substituent selected from the group consisting of halogen, cyano, $C_1$–$C_4$ alkyl and $C_1$–$C_4$ alkoxy;

or represents a thienyl, furyl, tetrahydrofuryl, pyridylmethyl or pyridylethyl radical;

or represents a phenyl radical which is unsubstituted or substituted by one or more substituents selected from the group consisting of halogen, cyano, $C_1$–$C_4$ alkyl and $C_1$–$C_4$ alkoxy; or $R^1$ and $R^2$ together with the nitrogen atom to which they are bonded represent a pyrrolidino, piperidino, piperazino or morpholino radical which is unsubstituted or substituted by up to 4 methyl groups;

$R^3$ represents $C_1$–$C_4$ alkyl which is unsubstituted or substituted with one or more substitutents selected from the group consisting of hydroxyl, halogen, cyano, $C_1$–$C_4$ alkoxy, aminocarbonyl and $C_1$–$C_4$ alkoxycarbonyl;

or represents an allyl radical;

or represents a benzyl or phenethyl radical each of which is unsubstituted or substituted by one or more substituents selected from the group consisting of halogen, $C_1$–$C_4$ alkyl, and $C_1$–$C_4$ alkoxy;

$R^4$ represents hydrogen or $C_1$–$C_4$-alkyl;

$R_5$ represents $SO_2R_{10}$ or $COR^{11}$;

$R^6$ and $R^7$, independently of one another each represent hydrogen, $C_1$–$C_4$ alkyl, $C_1$–$C_4$ alkoxy or halogen, $R^8$ represents a $C_1$–$C_4$ alkyl radical which is unsubstituted or substituted by one or more substituents selected from the group consisting of hydroxyl, halogen, cyano, $C_1$-$C_4$ alkoxy, aminocarbonyl and $C_1$-$C_4$ alkoxycarbonyl;

or represents an allyl, cyclopentyl or cyclohexyl radical;

or represents a benzyl, phenethyl or phenyl radical, each of which is unsubstituted or substituted by one or more substituents selected from the group consisting of halogen, $C_1$-$C_4$-alkyl, $C_1$-$C_4$-alkoxy, $C_1$-$C_4$-acylamino and hydroxyl;

or represents a thienyl, furyl, tetrahydrofuryl, pyridyl, pyridylmethyl, pyridylethyl radical;

$R^9$ represents hydrogen;

or represents a $C_1$-$C_4$-alkyl radical which is unsubstituted or substituted by one or more substituents selected from the group consisting of hydroxyl, halogen, cyano, $C_1$-$C_4$ alkoxy, aminocarbonyl and $C_1$-$C_4$ alkoxycarbonyl;

or represents an allyl, cyclopentyl or cyclohexyl radical;

or represents a benzyl, phenethyl or phenyl radical, each of which is unsubstituted or substituted by one or more substituents selected from the group consisting of halogen, $C_1$-$C_4$-alkyl, $C_1$-$C_4$-alkoxy, $C_1$-$C_4$-acylamino and hydroxyl;

or represents a thienyl, furyl, tetrahydrofuryl, pyridyl, pyridylmethyl, pyridylethyl radical; or $R^8$ and $R^9$ together with the nitrogen atom to which they are attached represent a pyrrolidino, piperidino, piperazino, morpholino or pyrazolino radical which is unsubstituted or substituted by up to 4 methyl groups;

$R^{10}$ represents a hydrogen or $C_1$-$C_8$ alkyl which is unsubstituted or substituted by one or more substituents selected from the group consisting of hydroxy, halogen, $C_1$-$C_4$-alkoxy, and cyano;

or represents $C_2$-$C_4$ alkenyl, cyclopentyl or cyclohexyl;

or represents a benzyl or phenyl radical each of which is unsubstituted or substituted by a substituent selected from the group consisting of halogen, cyano, $C_1$-$C_4$ alkyl and $C_1$-$C_4$ alkoxy;

or represents a thienyl or pyridyl radical;

or represents O-$C_1$-$C_8$-alkyl;

or represents a benzyloxy or phenyloxy radical, each of which is unsubstituted or substituted with one or more substituents selected from the group consisting of halogen, cyano-, $C_1$-$C_4$ alkyl and $C_1$-$C_4$ alkoxy;

$R^{11}$ represents a hydrogen or $C_1$-$C_8$ alkyl which is unsubstituted or substituted by one or more substituents selected from the group consisting of hydroxy, halogen, $C_1$-$C_4$-alkoxy, and cyano;

or represents $C_2$-$C_4$ alkenyl, cyclopentyl or cyclohexyl;

or represents a benzyl or phenyl radical each of which is unsubstituted or substituted by a substituent selected from the group consisting of halogen, cyano $C_1$-$C_4$ alkyl and $C_1$-$C_4$ alkoxy;

or represents a thienyl or pyridyl radical;

or represents O-$C_1$-$C_8$ alkyl;

or represents a benzyloxy or phenyloxy radical, each of which is unsubstituted or substituted with one or more substituents selected from the group consisting of halogen, cyano-, $C_1$-$C_4$ alkyl and $C_1$-$C_4$ alkoxy;

or represents $NHR^{11}$, and $X^\ominus$ represents an anion.

2. Cationic 1,3,4-thiadiazole dyestuffs according to claim 1, characterised in that in formula (I)

$R^1$ and $R^2$, independently of one another, denote methyl, ethyl, propyl, butyl, hydroxyethyl, hydroxypropyl, cyanoethyl, methoxyethyl or ethoxyethyl or $R^1$ and $R^2$, together with the nitrogen atom in between, denote morpholino, $R^3$ denotes methyl, ethyl, hydroxyethyl, hydroxypropyl or cyanoethyl, $R^4$ denotes hydrogen, $R^5$ denotes $COR^{11}$, $R^6$ denotes methyl, chlorine or methoxy, $R^7$ denotes hydrogen, $R^8$ denotes phenyl, methylphenyl, dimethylphenyl, tert.-butylphenyl, chlorophenyl, dichlorophenyl, methoxyphenyl, hydroxyethoxyphenyl, cyanophenyl or acetaminophenyl, $R^9$ denotes hydrogen, $R^{11}$ denotes methyl or ethyl and $X^\ominus$ denotes a colourless anion.

3. Anhydro base of the formulae

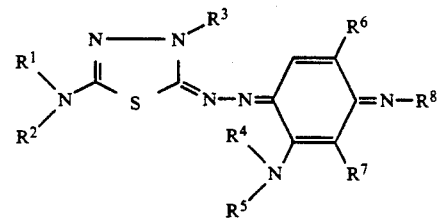

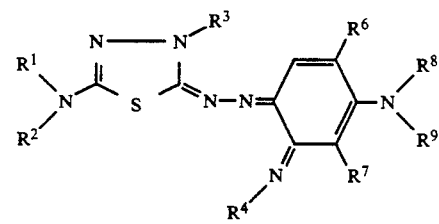

in which $R^1$ to $R^9$ have the meaning given in claim 12.

4. Process for the dyeing and printing of cationic dyeable fibres, cellulose materials treated with tannic acid, paper, silk and leather, and for the preparation of pastes for ball-point pens, writing and stamping inks and in flexographic printing with a dyestuff wherein a cationic 1,3,4-thiadiazole dyestuffs of claim 1 is used.

5. Cationically dyeable fibres, cellulose materials treated with tannic acid, paper, silk, leather, pastes for ball-point pens, writing inks and stamping inks, characterised in that they contain at least one cationic 1,3,4-thiadiazole dyestuff of claim 1.

* * * * *

UNITED STATES PATENT AND TRADEMARK OFFICE
CERTIFICATE OF CORRECTION

PATENT NO. : 5,208,325

DATED : May 4, 1993

INVENTOR(S) : Berneth, et al.

It is certified that error appears in the above-identified patent and that said Letters Patent is hereby corrected as shown below:

Col. 30, line 50    Delete " claim 12 " and substitute
                    -- claim 1 --

Signed and Sealed this

Twenty-second Day of November, 1994

Attest:

BRUCE LEHMAN

*Attesting Officer*    *Commissioner of Patents and Trademarks*